United States Patent
Steiner et al.

[11] Patent Number: 5,851,106
[45] Date of Patent: Dec. 22, 1998

[54] PORTABLE FAN DEVICE

[75] Inventors: Gregory A. Steiner, Lombard; Terry Arnieri, Addison, both of Ill.

[73] Assignee: Innovative Design Enterprises, Inc., Addison, Ill.

[21] Appl. No.: 24,729

[22] Filed: Feb. 17, 1998

[51] Int. Cl.[6] .............................. B63H 1/00; A47C 7/74; F04B 17/00
[52] U.S. Cl. .................. 416/63; 416/146 R; 417/411
[58] Field of Search .................. 416/63, 146 R, 416/142 R, 246, 244 R; 417/234, 411

[56] References Cited

U.S. PATENT DOCUMENTS

| | | | |
|---|---|---|---|
| 1,254,042 | 1/1918 | Howe | 416/63 X |
| 1,473,045 | 11/1923 | Puttaert et al. | 416/146 X |
| 2,595,406 | 5/1952 | Popovich | 417/411 X |
| 2,750,104 | 6/1956 | Scaroulis | 417/411 |
| 2,909,316 | 10/1959 | Prohaczka et al. | 416/63 |
| 3,099,386 | 7/1963 | Pieper | 417/411 X |

FOREIGN PATENT DOCUMENTS

| | | | |
|---|---|---|---|
| 2161304 | 6/1973 | Germany | 417/411 |

*Primary Examiner*—John E. Ryznic
*Attorney, Agent, or Firm*—Basil E. Demeur; Alan B. Samlan; Robert L. Knechtel

[57] ABSTRACT

There is disclosed an elongate style portable fan device having an elongate body portion including a fan device mounted on the top end of the body portion. The elongate body portion is designed to lay flat on an underlying flat surface in a manner which maintains the fan device portion at an angle of approximately 30 degrees from the central horizontal axis of the elongate body portion such that the fan blades of the fan device are free to rotate above the underlying flat surface when in the fan activated mode. The elongate body portion includes stop means for providing a resting stop position for the elongate body portion in order to permit the fan blades of the fan device to rotate freely when in the resting position and in the fan activation mode while laying on a flat underlying surface. Switch means is provided to the device for alternating between a fan activation and a fan deactivation mode. A scented pad added to the device and positioned so that rotating fan blades will disseminate the scent emanating from the scent pad.

13 Claims, 2 Drawing Sheets

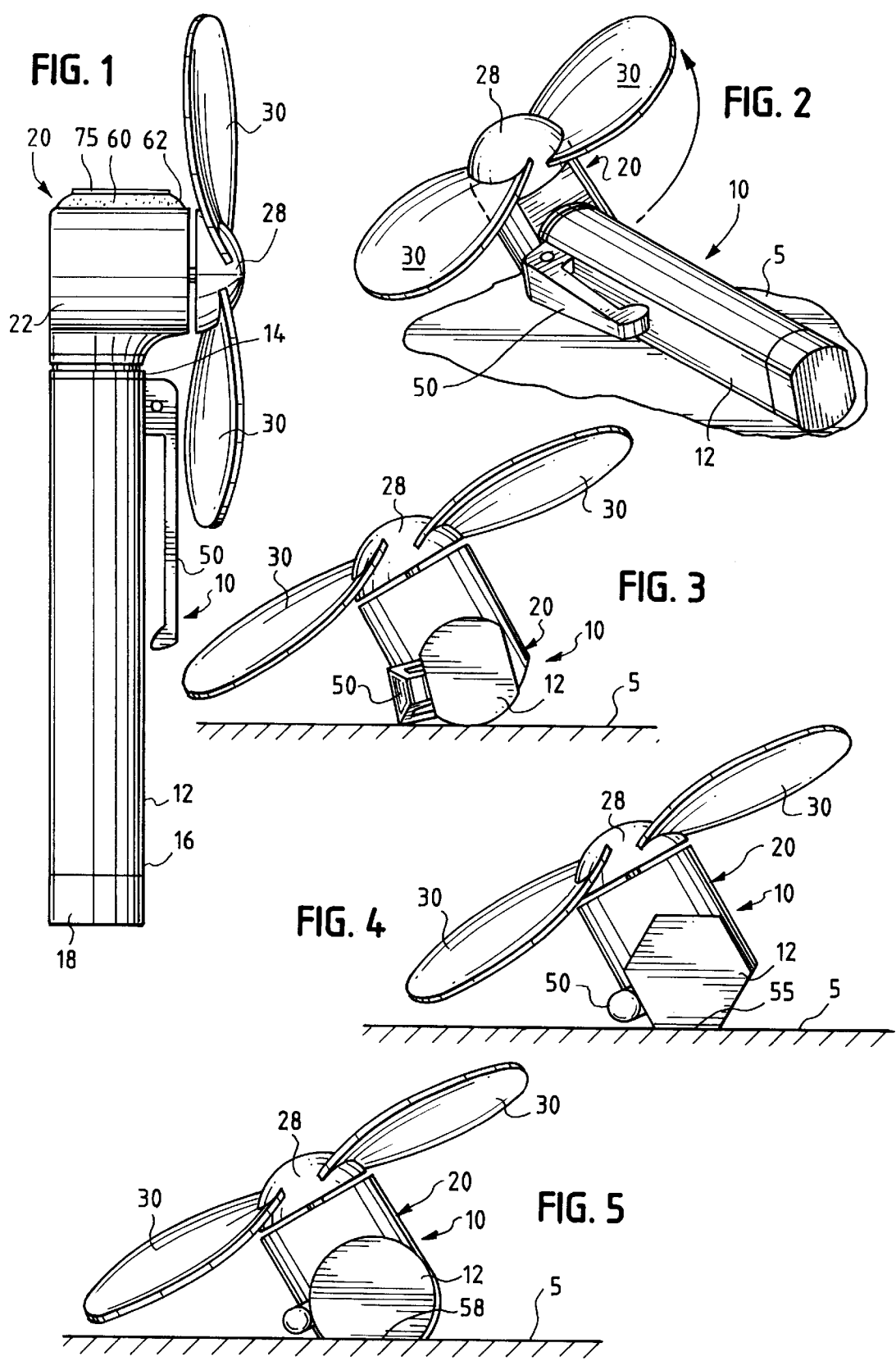

PORTABLE FAN DEVICE

BACKGROUND OF THE INVENTION

The art field relative to portable electric fans is well established. Any number of portable fans have been developed and exist for a variety of applications depending upon the use to which the user intends to apply the fan. In most instances, such portable fans are battery operated, and are basically designed much like flashlights having an elongate body for forming a battery chamber, and having a fan device attached either at the top of the device, or having the fan device sitting on the top side of the unit and facing outwardly in a 90 degree angle relative to the handle case.

In most instances, such portable fans are intended to be held by the user by griping the elongate body portion since that portion is usually designed as a battery chamber, and forms a convenient handle for the user. One such version of a portable fan has been in commercial production for a number of years consists of a short elongate body forming a battery chamber and having a reciprocating switch located thereon, and has a pair of collapsible fan blades mounted to a fan hub at the top of the unit. The operator grips the device by griping the elongate body portion which forms a handle, and when activating the switch, activates the fan motor which then turns the fan hub causing the fan blades to pivot outwardly and form a cooling fan device. This type of unit has been commercially available for a number of years.

Other types of cordless fans have been produced and generally include a fan unit which, in the usual application, provides a plurality of fan blades encased within a cage unit, with the entire unit being provided with a stand of some type for seatment upon an underlying surface. The stand usually takes the form of a base upon which the fan unit is mounted, the base being adapted for seatment upon a flat surface such as a table top or the like. Such types of devices may either be made with battery power for portability, or are provided with an electrical cord for engagement with an electrical system.

The present invention is intended to be an improvement in connection with portable hand held fan units which have the adaptability and capacity to be laid down on a flat underlying surface for the purpose of expanding the usage and application of such a unit.

OBJECTS AND ADVANTAGES

The principal object of the present invention is to provide a portable fan device which may be utilized either as a hand held unit, or may be laid on a flat underlying surface and placed into a fan activation mode with the fan unit portion of the device being adapted for rotational movement in a manner wherein the fan blades are freely rotatable for the purpose of cooling the user, while lying on an underlying flat surface.

In conjunction with the foregoing object, it is a further object of the present invention to provide a portable fan device of the type described which is formed by an elongate body portion having a top end and a bottom end, and having a central horizontal axis along the length of the body portion. A fan device is mounted at the top end of the elongate body portion. Stop means are associated with the elongate body portion in order to provide a resting stop position for the elongate body portion when resting on a flat underlying support surface. Stop means cooperates with the elongate body portion and is in further synchronization with the fan unit such that when the device is laid on a flat underlying surface along its horizontal axis, the fan blades associated with the fan device are free to rotate when in the fan activation position without interference by the underlying support surface, and thereby permits the device to be laid flat on a surface and activated so that the fan can perform its cooling function.

In furtherance of the above objects and advantages, the present device may further be designed in the preferred embodiment to provide a head portion which includes a housing containing a fan motor and having a motor shaft extending outwardly therefrom, and having a fan hub mounted on the motor shaft and the fan hub including at least two fan blades carried thereon. The entire head portion is adapted to be rotationally moveable relative to the elongate body portion by rotating the fan head throughout an angle of approximately 360 degrees, and the head portion and elongate body portion each respectfully include switch contacts such that upon rotation of the head portion through an angle of about 90 degrees, the switch contacts close to establish a fan activation position and energize the fan blades to freely rotate. The unit is designed such that upon rotation of the head unit through an angle of approximately 90 degrees, the entire head unit including the fan blades are positioned free of the underlying support surface when the unit is laid flat on a surface such that they are free to rotate in order to perform the cooling function.

In connection with the foregoing object, it is a further object of the present invention to provide a fan device of the type described wherein the housing forming the head portion is provided with a sloped cap portion formed on the backside thereof in opposed relation to the positioning of the fan blades, the sloped cap providing a rest stop position when the unit is laid flat on an underlying support surface. The sloped cap thereby provides a resting position when the fan device is laid horizontally flat on an underlying support surface and will maintain the head portion in a space position approximately 30 degrees from the horizontal axis of the elongate body portion in a manner such that the fan blades are freely rotatable relative to the underlying support surface when in the fan activation position.

A further embodiment of the present invention contemplates the elongate body portion may be formed in a geometric shape which includes at least one flat surface formed along the horizontal axis thereof such that the flat surface forms the stop means for providing a resting stop position of the unit when laying flat on an underlying flat surface, the flat portion of the elongate body portion being positioned such that when the fan unit is at a 30 degree angle relative to the horizontal axis of the fan device, the blades are free to rotate when in the fan activation mode and when the unit is lying flat on an underlying support surface.

In other embodiments of the invention, it is contemplated that the stop means associated with the elongate body portion may be formed by a combination of the geometric shape of the elongate body portion in combination with a fastening clip such that the geometric shape of the elongate body portion provides a surface for the fan device to lay against when lying on an underlying support surface, and the fastening clip providing a stop position to maintain the unit in a substantially horizontal position with the fan blades of the fan device positioned at an angle of approximately 30 degrees from the horizontal axis of the device in order to permit the blades to be freely rotatable.

As a further object of the present invention, it is contemplated that the present invention may include a scented pad or stick which may be installed on the top portion of the head unit, and spaced rearwardly of the fan blades, such that when the fan blades are activated into the fan activation position, and the fan rotates, any desired scent as incorporated in the scent pad will be picked up by the fan and result in a scented breeze emanating from the fan unit when activated.

The above objects and advantages as well as additional objects and advantages will be realized by reference to the following specification taken in conjunction with the accompanying drawings.

SUMMARY OF THE INVENTION

In summary, the present invention provides an improved portable fan device which is intended to be utilized either as a hand held unit by the user, or may be laid on a flat underlying surface and activated and permitting the fan blades to rotate freely while lying in a flat position on such surface. In the preferred embodiment, the switch means associated with the device are designed by providing switch contacts in a rotatable head unit, as well as the elongate body portion, such that the head unit, when rotated through an angle of between 30 and 90 degrees, will close the switch contacts, thereby to energize the fan device causing the fan blades to rotate. The device is further designed such that once it is in the fan activation mode, the entire head unit, and especially the fan blades are freely rotatable, free and clear of the underlying flat surface upon which the device lies, and thereby permits the user to enjoy the cooling effects of the device without the necessity of constantly holding the device and aiming the device at the user's body.

A further feature of the preferred embodiment of the invention is to provide a portable fan device of the type described which may further be provided with a scented pad or stick located at the upper end of the unit and affixed to the top of the fan head portion such that when the fan is activated, the scent incorporated in the scented pad will be picked up by the fan as it rotates, thereby to create a scented breeze for the benefit of the user. In this manner, the device may also be utilized as an air freshening device by the user thereof.

The invention, both as to its organization and method of operation, together with further objects and advantages thereof, will best be understood by reference to the following specification taken in connection with the accompanying drawings.

BRIEF DESCRIPTION OF DRAWINGS

FIG. 1 is a side elevational plan view showing the portable fan device of the present invention;

FIG. 2 is a perspective view showing the fan device of the present invention in its application when laid on a flat underlying surface with the fan blades being freely rotational when in the resting stop position;

FIG. 3 is an end elevational view of the fan device of the present invention as shown in FIG. 2, and illustrating the stop means for maintaining a resting stop position of the unit when laying on an underlying flat surface in a manner which maintains the blades in a freely rotational mode;

FIG. 4 is an end elevational view showing an alternate embodiment of the present invention wherein the elongate body portion is formed as a hexagonal geometric shape, which includes a flat portion in order to provide a flat surface which in turn provides a resting stop position for the unit when lying on an underlying flat surface and maintaining the blades in a freely rotational activation mode;

FIG. 5 is an end elevational view showing still another embodiment of the present invention wherein the elongate body portion is shown as a substantially circular geometric shape having one flat portion in order to form a resting position for the unit when lying on an underlying flat surface and maintaining the fan blades in a freely rotational activation mode.

DETAILED DESCRIPTION OF DRAWINGS

Figure 6:
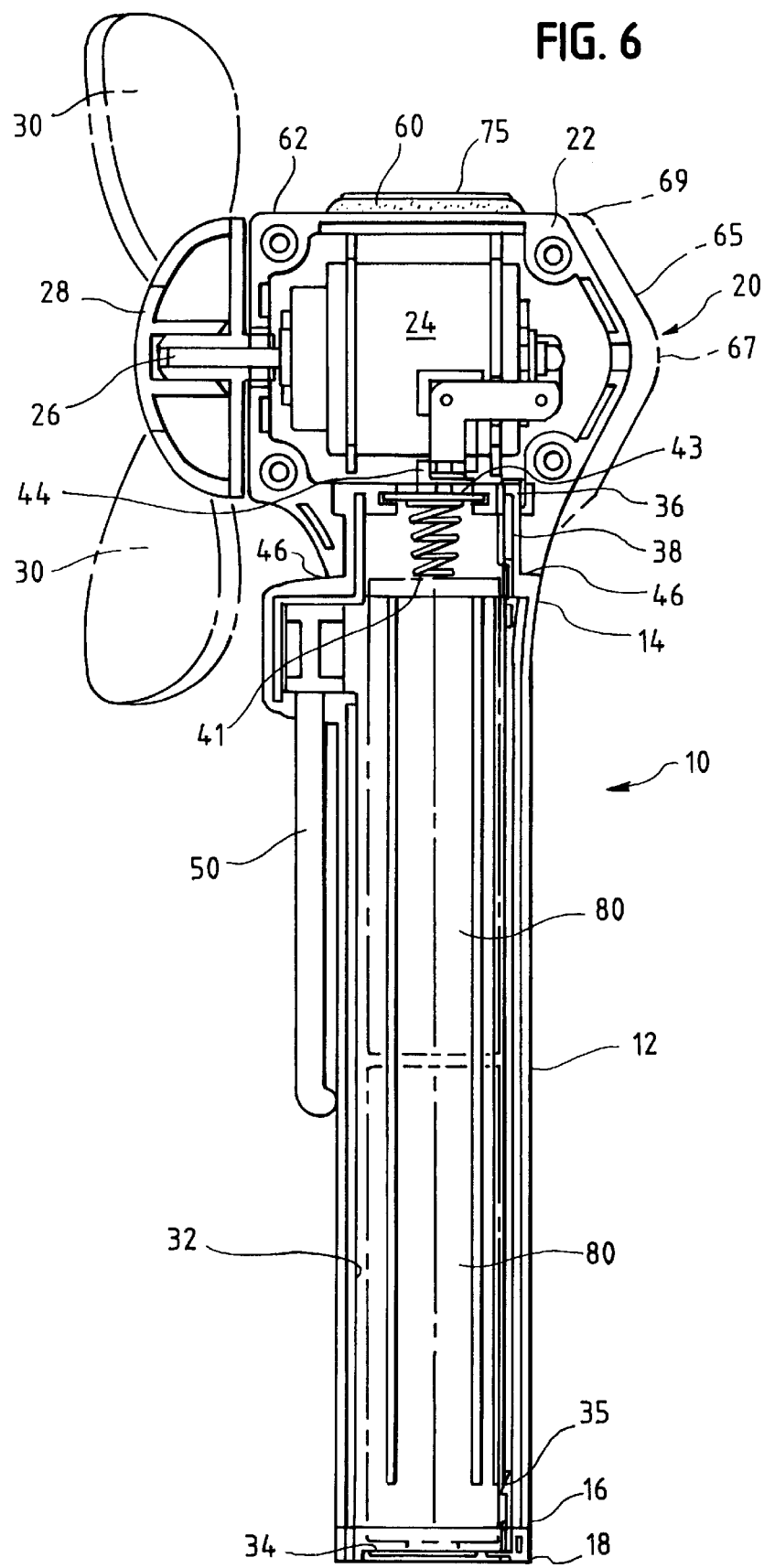
FIG. 6 is a side elevational view, in cross section, showing the fan device of the present invention and its manner of construction and operation including an alternative stop means consisting of a sloped cap portion formed on the back side of the head unit and functions as a stop means when the device is in a horizontal position and maintains the blades in a freely rotational mode when in the fan activation position.

With reference to the drawings, the fan device is generally represented by the numeral 10. The fan device 10 is formed by the elongate body portion 12, which forms a convenient grasp section for the hand of a user, in a manner which is well-known in the art. For ease of description, similar reference numerals will be utilized for the same body portion relative to each of the embodiments described hereinafter.

The elongate body portion 12 includes a top end 14 and a bottom end 16, the bottom end 16 being enclosed by a bottom lid 18 (See FIG. 6). As is well-known and understood from common flashlights, the bottom lid 18 is intended to enclose the bottom end 16 of the elongate body portion 12 and encloses the battery chamber in a manner which will be more fully described hereinafter.

The top end 14 of the elongate body portion 12 is provided with a head portion 20, which is the portion providing the cooling effect of the unit device 10. It will be observed that the head portion 20 is formed by a housing 22 which carries a fan motor 24 which is, in turn, provided with a fan shaft 26, extending outwardly therefrom, and, in turn, carries a fan hub 28 mounted thereon, the fan hub carrying two fan blades 30 (See FIG. 6). It is contemplated that any number of fan blades may be employed depending upon the space limitations dicated by the packaging and the cooling effect desired. The present invention contemplates at least a pair of fan blades as demonstrated. In the preferred embodiment as contemplated by the present invention, the fan blades 30 are made of a flexible material such as Ethyl Vynyl Acetate Foam material, which is soft and non-obtrusive to the human flesh should the fan blades 30 strike against the human body. While the drawings and the present description illustrate the preferred embodiment of the invention, it is clear that the fan device may consist of a fan unit which is formed by a plurality of stiff blades, preferably of plastic, and surrounded by a cage in order to prevent any harm or injury to the user thereof. It is contemplated that the preferred embodiment would include blades made from a soft and non-obtrusive material in order to eliminate the cage element from the device, but the incorporation of stiff blades with a cage is contemplated to be within the purview of the present invention.

As previously indicated, the bottom lid 18 is intended to fit onto the bottom end 16 of the elongate body portion 12 either by screw threadedly engaging thereon, or by some form of press fit. This type of arrangement is well-known in connection with common flashlights which are well-known in the state of the art.

The elongate body portion 12 is shown to form a battery chamber 32 in order to carry a pair of batteries 80 in a manner well-known in the art in connection with common flashlight cases and batteries contained therein. The bottom lid 18 is provided with a metal contact plate 34 and has an upwardly extending contact arm 35 which extends up along the entire length of the elongate body portion 12 terminating in a positive motor contact 36 to which the positive terminal of the fan motor 24 is connected. The elongate body portion 12 includes an upper neck portion 38 in which is carried a metal coil spring 41 which, in use, is interposed between the bottom or negative terminal of the battery 80, and a contact plate 43. The contact plate 43 is provided with an upstanding negative contact terminal 44 which, in use, will contact the negative terminal of the fan motor 24 when in its proper activation position.

In the preferred embodiment as illustrated in the present drawings, the switch means for the device 10 is formed by providing a head portion 20 which is rotationally moveable relative to the elongate body portion 12. As shown in FIG. 6 of the drawing, the head portion 20 rotates about the sheer line 46, with the head portion 20 designed to rotate approximately 90 degrees relative to the horizontal plane of the elongate body portion 12. This is more aptly illustrated in FIGS. 2 through 5 of the drawings. It will be appreciated that both the positive contact plate 36 and negative contact terminal 44 are positioned such that upon rotation of the head portion 20 through a 90 degree angle to the "on" position, the contact plates come into registry with one another in order to provide electrical energy from the batteries 80 to the fan motor 24 thereby activating the motor 24 causing the fan hub 28 and therefore the fan blades 30 to rotate. It is believed that the particular operation of the contacts relative to the motor is well-known in the art in connection with a variety of battery operated devices. It is further contemplated that the electrical portion of the device contemplated by the present invention is not deemed to be a part of the invention herein apart from the entire device as illustrated.

Once again, the device as illustrated in the accompanying drawings and as described hereinabove relates to the preferred embodiment of the invention, wherein the head portion 20 is constructed to rotate to provide and on/off switching means for switching the fan on and off respectively. In the preferred embodiment, there is a single "on" position which when the head portion 20 is rotated to the "on" position, the fan unit will operate, and in this position, the head unit will be approximately 30 degrees above the horizontal axis of the elongate body portion 12 in order that the fan blades may be free and clear of the underlying support surface upon which the unit rests. However, it is contemplated that the device of the present invention may be made with a stationary head, indeed formed as a single piece with the elongate body portion, and a simple on/off switch provided for the unit in order to activate and deactivate the fan motor. The unit will operate so long as stop means are provided so that when the unit is laid in its flat horizontal position on an underlying flat support surface, the fan blades are maintained above the surface of the underlying flat support surface so that the blades are freely rotational. For example, it is contemplated that a fan device in accordance with FIG. 6 may be constructed as a complete fan unit, which would include the sloped cap portion 65 on the back side of the head unit which thereby functions as a stop position for the whole unit while lying in a horizontal flat position on an underlying support surface. A simple on/off switch may be provided so that the unit may be activated in order to rotate the fan blades. In such an embodiment, the fan blades would be positioned approximately 30 degrees above the horizontal so as to be freely rotational when activated and when lying in the flat disposition.

The fan device 10 as illustrated is shown further to be provided with a fastening clip 50 which is mounted on the outer portion of the elongate body portion 12, as illustrated in the drawings. With specific reference to FIGS. 2 and 3 of the drawings, it will be observed that the elongate body portion is basically formed with a geometric shape consisting of semicircles at the top and bottom portions of the device, and opposed flats on the opposed side surfaces. The fastening clip 50 basically functions for the user to clip the device onto his apparel such as on a shirt pocket, but then, in use, will operate to provide a stop position as illustrated in FIGS. 2 and 3 of the drawings. It will be observed that when the fan device 10 is laid flat on an underlying flat surface 5, the fastening clip 50 provides a rest stop such that the device is stabilized on the flat surface 5. When the head unit 20 is turned to the on position, this is accomplished by rotating the head portion through approximately a 90 degree angle relative to the horizontal axis of the elongate body portion 12. This is generally referred to herein as the activation mode for the fan motor 24 since in this mode, the fan motor is activated thereby to cause the fan blades 30 to rotate. As will be observed in FIGS. 2 through 5 of the drawings, when in the "on" position, the fan blades 30 are free to rotate free and clear of the underlying flat surface 5 thereby to provide the cooling function intended by the fan device 10.

It will be appreciated from a view of FIGS. 2 through 5 of the drawings, that the fan unit of the present invention may therefore be employed as a cooling device by the user thereof, without the necessity or need for the user to hold the device by the elongate body portion 12 in order to aim the device at his body for cooling purposes. With the present invention, the fan device 10 may be laid on a flat surface such as a desk top, and once the head portion 20 is turned to the on position, that is, by rotating through a 30 degree angle, the fan motor is activated to cause the fan blades 30 to turn and the user may then turn the device toward the user in order to achieve the cooling affect. Hence, it will be appreciated that the device need not be held by the user in order to effect a cooling as intended by the unit.

As further illustrated in FIGS. 1 and 6 of the drawings, the fan device 10 of the present invention may further be provided with a scented pad 60 which is affixed to the top end 62 of the head portion 20. It is contemplated that the scented pad 60 may be provided with a tacky or adhesive under surface in order to permit the user thereof to simply adhesively apply the scented pad 60 to the top of the unit. The scented pad may include any desired scent, and it is contemplated that when installed in position, and the fan blades 30 are operational, the scent from the scented pad 60 will be picked up by the fan blades 30, and provide an air freshening effect for the user. Indeed, it is contemplated that a package containing various different scented pads may be provided with the unit and permit the user to select any particular scent, and prior to using the fan device 10, simply applies the scented pad 60 of choice to the top of the unit and adhesively applies the same thereon, and prepares the unit for use.

For purposes of the present invention, the scented pad 60 may take the form of a scented stick, which is otherwise known in the art. The mode of attachment of the scented pad 60 or stick to the unit may vary, and hence, the pad or stick may be adhesively secured to the unit, or any other fastening means utilized. Furthermore, it is not critical that the scented pad 60 be affixed immediately behind the fan blades 30, but may be affixed in any position where air currents created by the fan blades may quickly and conveniently distribute the scent when the fan blades are rotating.

It is further contemplated that a shield materials such as a wax cover 75 (FIG. 1) may be employed as a cover over the scented pad 60 in order to minimize evaporation of the scent from the pad. Alternatively, a was filled material with a low temperature melting point may also be utilized in order to minimize evaporation of the scented oil or liquid contained in the pad or stick. Such wax filled scent sticks are activated by heat from the user's hand, in order to melt a portion of the wax and release the scent prior to use. Wax filled scented sticks having a low temperature melting point are known in the art and are employed for other purposes but will function adequately within the frame work of the present invention.

FIG. 6 further shows the unit in a preferred embodiment, wherein the stop means associated with the fan device 10 is provided by means of a sloped cap 65 which terminates in a peak 67 formed on the back side of the head portion 20. The sloped cap 65 in combination with the peak 67 provides a rest stop position for the entire unit when lying in a horizontal position on an underlying flat surface and will maintain the fan blades 30 in a freely rotational position when the unit is activated. This construction may be employed regardless of whether the fan device 10 is made with a rotational head portion 20, or in the event that the entire unit is made with the head portion merely being the upper part of the device, and an on/off switch is provided for activating the fan motor and blades. As has been indicated, however, the preferred embodiment of the invention would include a head portion 20 which is rotatable and incorporates the electrical contacts therein thereby to provide an on/off switch mechanism for energizing the motor and fan blades 30 in order to operate the device. The sloped cap 65 would thereby provide a rest stop position for the unit when lying horizontally flat on an underlying surface, and permit the fan blades 30 to rotate freely when activated.

It is contemplated and anticipated that the unit may be constructed in a manner wherein the head unit is integral with the elongate body portion and permanently secured at an angle such that when a rest stop position is formed for the unit to lay on a flat surface, the unit may be provided with an alternate switch device much like a flashlight, in order to activate the device an energize the fan motor. In such an event, the head unit or head portion of the unit would not be rotational, but would be permanently secured in a proper angle so that the fan blades are freely rotational relative to the underlying support surface. In such event, and as indicated, a separate switch would have to be provided in order to energize the device in order to provide electrical power from the batteries to the fan motor. It is contemplated that a device so constructed is fully within the spirit and scope of the present invention. However, for ease of manufacture and economics in construction, the preferred embodiment of the present invention contemplates incorporating the switch contact plates in the device with a rotating head portion in order to avoid the cost of providing a separate switching mechanism. Hence, in the preferred embodiment, the rotating head in effect is the switch device for the present invention.

It is further observed from the view of FIGS. 4 and 5 of the drawings that the elongate body portion may also be formed from a geometric shape which includes a flat portion in order to provide a resting stop position. For example, in FIG. 4, the elongate body portion 12 is shown to be formed in the shape of a hexagonal shape and includes a flat portion 55 which is designed relative to the head portion 20 such that when the head portion 20 is in the on or activated position, the flat portion 55 will function as a resting stop position. It will be observed that the fastening clip 50 need not be designed to coordinate with the body portion in order to provide a resting stop position, although the same may also provide an additional positive stop for the device if desired. As shown in FIG. 4, of the drawings, it is contemplated that the flat side 55 when properly designed relative to the head portion 20 provides a sufficiently stable surface such that the device will lay flat when the fan unit is activated and the fan blades are rotating.

As shown in FIG. 5 of the drawings, the elongate body portion 12 may be designed as a circular body portion, including a flat side 58 which, again, provides a stable resting stop position for the device such that when the head portion 20 is turned to the on position and the fan blades activated, will provide a stable rest position enabling the user to rest the device on a flat surface and point the fan at the user to achieve the cooling affect without holding the device.

It will be appreciated from the above description that the present invention provides a portable fan device which is intended to be small enough to be carried by a user such as in a pocket or the like, while nevertheless, being useable as a cooling device by the user holding the device in his hand, and aiming the fan portion at his body, or lying the device on a flat underlying surface and pointing the device at his body while turning the unit on and pointing the fan at the user eliminating the need for the user to hold the device.

While there has been described what is at present considered to be the preferred embodiments of the invention, it will be understood that various modifications may be made therein and it is intended to cover in the appended claims all such modifications as fall within the true spirit and scope of the invention.

We claim:

1. A portable fan device adapted for seatment on an underlying flat surface comprising, an elongate body portion having a top end and a bottom end and having a central horizontal axis along the length of said elongate body portion, said elongate body portion forming an elongate chamber, a fan device mounted on the top end of said elongate body portion, said fan device having an off position and a fan activation position associated therewith, stop means associated with said elongate body portion, said stop means adapted to maintain said elongate body portion in a rest position when said body portion is positioned on an underlying flat surface, along the horizontal axis of said elongate body portion, said fan device including a central hub and at least a pair of fan blades mounted to said hub and adapted for rotational movement when in the fan activation position, said fan device being positioned at an angle spaced from said central horizontal axis a distance sufficient to allow fan blade rotation when said elongate body portion is maintained by said stop means in a rest position on an underlying flat support surface, said elongate chamber accommodating electrical power means for providing energy to said fan device, and on/off switch means interposed between said fan device and said electrical power means to accommodate a fan off position and a fan activation position.

2. The portable fan device as set forth in claim 1 above, wherein said fan device includes a fan motor having a motor shaft extending outwardly therefrom, and having a fan hub mounted on said motor shaft, said fan hub including at least two fan blades carried thereon, and said fan device adapted to be positioned at an angle spaced from the horizontal axis of said elongate body position when said fan device is in a resting stop position on an underlying flat surface to accommodate the free rotation of said fan blades when said fan device is in a fan activation position.

3. The portable fan device as set forth in claim 2 above, wherein said elongate body portion is provided with a fastening clip secured thereto along the horizontal axis thereof, said fastening clip being positioned in cooperating relationship with said elongate body portion thereby to provide a resting stop position when said elongate body portion is lying horizontally on an underlying flat surface along its horizontal axis, and further arranged to maintain said fan blades above said underlying support surface in a freely rotatable position when in the resting stop position and in the fan activation position.

4. The portable fan device as set forth in claim 3 above, wherein said elongate body portion has a geometric shape include at least one flat surface formed along the horizontal axis thereof, said flat surface cooperating with said fastening clip thereby to provide a resting stop position for said fan device when lying on an underlying flat surface along its horizontal axis, said resting stop position being adapted to accommodate the fan blades being in a freely rotatable position when in the resting stop position and in the fan activation mode.

5. The portable fan device as set forth in claim 3 above, wherein said elongate body portion is formed in a geometric shape comprising a hexagonal shaped elongate body portion having one flat surface positioned such that said fan device, when positioned in the resting stop position on an underlying support surface and in the fan activation mode is approximately 30 degrees from the horizontal axis of said elongate body portion and permits said fan blade to be freely rotatable when in the fan activation position.

6. The portable fan device as set forth in claim 2 above, wherein said fan device mounted on the top end of said elongate body portion comprises a head portion consisting of a housing, a fan motor contained within said housing, said fan motor having a motor shaft extending outwardly therefrom, and having a fan hub mounted on said motor shaft, said fan hub including at least two fan blades carried thereon, said head portion being rotatable relative to said elongate body portion, said head portion and the elongate body portion each including switch contacts such that upon rotation of said head portion throughout an angle of approximately 30 degrees, said switch contacts close to establish the fan activation mode and energize said fan blades to freely rotate, said head portion in the fan activation mode being positioned a distance spaced from said horizontal axis of said elongate body portion when in the resting stop position to accommodate the free rotational movement of said fan blades when in the fan activation position.

7. The portable fan device as set forth in claim 1 above, wherein said fan device further includes scent means affixed to the top end of said fan device, said scent means providing scented air which may be transmitted to the user thereof via the rotation of the fan blades when in the fan activation mode.

8. The fan device as set forth in claim 7 above, wherein said scent means comprises a scented pad secured to the top end of said fan device by means of adhesive means, said scent pad providing scented air which may be transmitted to the user by the rotation of the fan blades when in the fan activation position.

9. The portable fan device as set forth in claim 1 above, wherein said fan device further includes a sloped cap positioned in opposed relation to said fan blades, said sloped cap providing a resting stop position for said portable fan device when lying on an underlying flat support surface along its horizontal axis and maintaining the fan blades in a position spaced from the underlying flat support surface in order to accommodate the free rotational movement of said fan blades when in the fan activation position.

10. A portable fan device adapted for seatment on an underlying flat surface comprising, an elongate body portion having a top end and a bottom end and having a central horizontal axis along the length of said elongate body portion, said elongate body portion forming an elongate chamber, a fan device mounted on the top end of said elongate body portion, said fan device having an off position and a fan activation position associated therewith, said fan device including a fan motor, and having a motor shaft extending outwardly therefrom, and having a fan hub mounted on said fan shaft and said fan hub including at least two fan blades carried thereon at the front end of said fan device, and having a rear end in opposed relation to said fan carrying front end, said rear end forming a sloped cap, said sloped cap cooperating with said elongate body portion thereby to provide a resting stop position for said elongate body portion when lying on an underlying flat support surface along the horizontal axis thereof and maintaining said fan blades in a freely rotatable position when in the fan activation position, said elongate chamber accommodating electrical power means for providing energy to said fan device, and on/off switch means interposed between said fan device and said electrical power means to accommodate a fan off position and a fan activation position.

11. The portable fan device as set forth in claim 10 above, wherein said fan device is formed as a head portion including a housing, a fan motor contained within said housing and having motor shaft extending outwardly therefrom and having a fan hub mounted on said motor shaft, said fan hub including at least two fan blades carried thereon, said head portion being rotatable relative to said elongate body portion, said head portion and elongate body portion each including switch contacts such that upon rotation of said head portion through an angle of at least 30 degrees, said switch contacts close to establish a fan activation position and energize said fan blades to freely rotate said fan devices lying on an underlying support surface and in the resting stop position along the horizontal axis thereof.

12. The fan device as set forth in claim 11 above, wherein said fan device further includes scented means adapted to be secured to said fan device and in operational proximity to said fan blades, said scented means providing scented air which is transmitted to the user thereof when the fan blades are in the fan activation position and rotating.

13. The fan device as set forth in claim 12 above, wherein said scented means comprises a scented pad secured to the top end of said fan device and spaced rearwardly of said fan blades, said scented means providing scented air which is transmitted to the user thereof when the fan blades are in the fan activation position and rotating.

* * * * *